United States Patent
Moceri et al.

(10) Patent No.: US 12,214,209 B2
(45) Date of Patent: Feb. 4, 2025

(54) EXTERIOR INSULATOR FOR AN IMPLANTABLE POWER SOURCE

(71) Applicant: Greatbatch Ltd., Clarence, NY (US)

(72) Inventors: Kenneth P. Moceri, Niagara Falls, NY (US); Louie Serpe, Clarence Center, NY (US); Alison M. Torregrossa, Alden, NY (US)

(73) Assignee: Greatbatch Ltd., Clarence, NY (US)

( * ) Notice: Subject to any disclaimer, the term of this patent is extended or adjusted under 35 U.S.C. 154(b) by 322 days.

(21) Appl. No.: 17/715,528

(22) Filed: Apr. 7, 2022

(65) Prior Publication Data

US 2022/0331595 A1 Oct. 20, 2022

Related U.S. Application Data

(60) Provisional application No. 63/175,811, filed on Apr. 16, 2021.

(51) Int. Cl.
*A61N 1/375* (2006.01)
*A61N 1/378* (2006.01)

(52) U.S. Cl.
CPC ........... *A61N 1/375* (2013.01); *A61N 1/3758* (2013.01); *A61N 1/378* (2013.01); *A61M 2205/8206* (2013.01)

(58) Field of Classification Search
CPC ...... A61N 1/375; A61N 1/3758; A61N 1/378; A61M 2205/8206
See application file for complete search history.

(56) References Cited

U.S. PATENT DOCUMENTS

| | | | | |
|---|---|---|---|---|
| 2003/0204216 A1* | 10/2003 | Ries | ................... | A61N 1/37512 607/36 |
| 2004/0064163 A1* | 4/2004 | Aamodt | ................. | A61N 1/378 607/36 |
| 2016/0129264 A1* | 5/2016 | Hovland | ............... | H01M 50/55 607/116 |

* cited by examiner

*Primary Examiner* — Eugene T Wu
(74) *Attorney, Agent, or Firm* — Michael F. Scalise (57) ABSTRACT

A polymeric film cover assembly for isolating an electrochemical power source from the other components housed inside an implantable medical device is described. The cover assembly comprises a first shallow-formed shaped-cover of a polymeric film configured to cover a first portion of the exterior surface of the casing and a second shallow-formed shaped-cover of the polymeric film configured to cover a second portion of the exterior surface of the casing. With the first and second shaped-covers contacting the casing, the shaped-covers are connected to each other in an overlapping or butted relationship to substantially or completely cover the exterior surface area of the casing. The interlocking polyester shaped-covers are readily formable into the desired three-dimensional form factor of the casing of power source while maintaining a desirable film thinness.

20 Claims, 5 Drawing Sheets

EXTERIOR INSULATOR FOR AN IMPLANTABLE POWER SOURCE

CROSS-REFERENCE TO RELATED APPLICATION

This application claims priority to U.S. provisional application Ser. No. 63/175,811, filed on Apr. 16, 2021.

BACKGROUND OF THE INVENTION

Field of the Invention

The present invention relates to the conversion of chemical energy to electrical energy. More particularly, the present invention relates to a polymeric film that covers the exterior surface of an implantable power source. The purpose of the film is to electrically isolate the power source from other components housed inside an implantable medical device. The polymeric film of the present invention is provided in two or more shaped-cover parts that are connected together to cover a desired portion or all of the exterior surface of the implantable power source.

Prior Art

An implantable power source such as an electrochemical cell or a capacitor often requires electrical isolation from other components within a finished implantable medical device. Exemplary implantable medical devices include, but are not limited to, a pacemaker, an implantable cardiac defibrillator (ICD) and a neurostimulator. Often a thin polyimide film with an adhesive is used for electrical isolation. To minimize the internal volume occupied by the electrochemical power source, it is desirable that the polyimide film be as thin as practical, for example, having a thickness of about 0.002 to 0.003 inches. However, since a thin polyimide film is not easily formable, the film is made in a flat/planar geometry that requires complex slitting and folding to provide adequate coverage of the three-dimensional shape of the implantable power source.

As an alternative, a formable polyester film can provide the necessary electrical insulation. However, in the requisite about 0.002 to about 0.003-inch thickness range, forming a single "cup" or "boot" in the size and profile shape of a typical electrochemical cell or capacitor is impractical.

Thus, there is a need for an improved electrical insulation design for electrically isolating a power source from the other components housed inside an implantable medical device. The present invention fulfills this need.

SUMMARY OF THE INVENTION

In order to obtain the desired thickness in a formable polymeric film supported on the exterior surface of the casing of a power source to electrically isolate the power source from the other components housed inside an implantable medical device, the current invention provides two or more "shallow-formed" and inter-locking shaped covers of polyester film. The inter-locking polyester shaped-covers are readily formable into the desired three-dimensional form factor for the insulation component while maintaining the desired film thinness.

The use of polyester film is in comparison to a parylene coating, which is difficult to apply to the exterior surface of the power source and easily damaged. Moreover, parts of the power source, such as the terminal pin that are not intended to be coated must be masked. However, removing the masking material after the power source has been coated can damage the terminal pin. Alternate materials such as a polyimide film with adhesive can be difficult to apply and often result in undesirable bubbles, creasing, and the like.

These and other aspects of the present invention will become increasingly more apparent to those skilled in the art by reference to the following detailed description and to the appended drawings.

DETAILED DESCRIPTION OF THE PREFERRED EMBODIMENTS

As described in this detailed description, it is understood that the casing for an electrochemical power source, for example, an electrochemical cell or a capacitor, has an exterior surface. The exterior surface of the casing has a surface area. The novel polymeric film cover assembly of the present invention, which will be described in detail hereinafter, substantially covers or substantially envelopes that exterior surface. The term "substantially covers" or "substantially envelopes" means that the polymeric film cover assembly covers greater than 50% of the exterior surface area of the casing, more particularly, greater than 65% of the exterior surface area of the casing, still more particularly, greater than 80% of the exterior surface area of the casing. Further, "substantially covers" or "substantially envelopes" means that the polymeric film cover assembly covers greater than 90% of the exterior surface area of the casing. Furthermore, "substantially covers" or "substantially envelopes" means that the polymeric film cover assembly covers up to 95% of the exterior surface area of the casing. Finally, "substantially covers" or "substantially envelopes" means that the polymeric film cover assembly covers the entire exterior surface area of the casing, leaving only the terminal pin extending outwardly from a glass-to-metal-seal and an outwardly extending casing connection for the other of the anode and the cathode not connected to the terminal pin uncovered.

Figure 1:
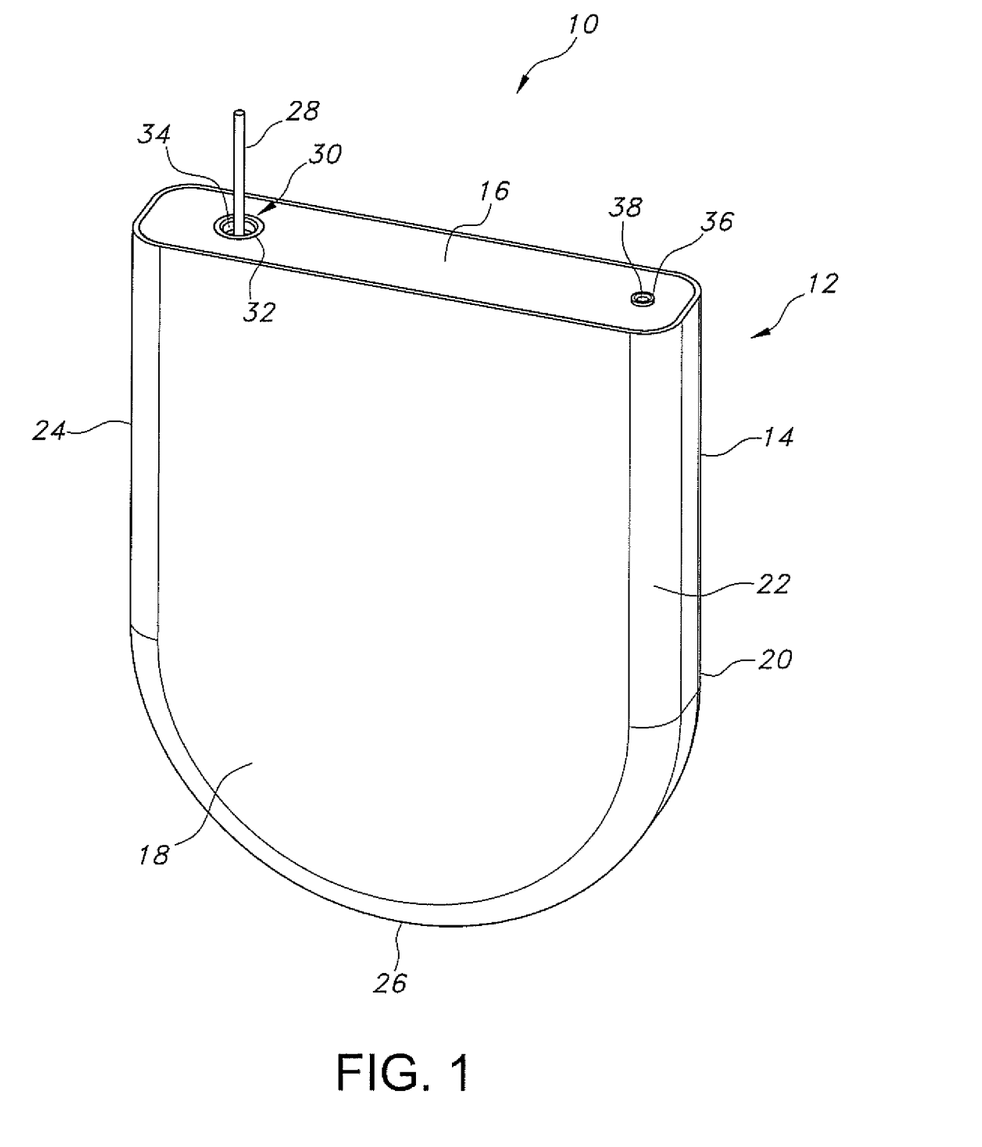
FIG. 1 is a perspective view of an exemplary prismatic electrochemical cell 10.

Turning now to the drawings, FIG. 1 illustrates an exemplary implantable power source 10, for example an electrochemical cell or a capacitor, that is useful with the present invention. The implantable power source 10 has an enclosure or casing 12 formed from an open-ended container 14 closed by a plate-shaped lid 16. The container 14 has spaced-apart front and back face walls 18 and 20 joined by curved end walls 22 and 24 and a curved bottom wall 26. The container 14 and lid 16 each have a thickness that ranges from about 0.010 inches to about 0.048 inches.

Those skilled in the art will readily understand that the power source 10 has an electrode assembly comprising an anode in electrochemical association with a cathode housed inside the casing 12. The anode and cathode are prevented from direct physical contact with each other by an intermediate separator. An exemplary electrochemical couple is a lithium/silver vanadium oxide (Li/SVO) or lithium/$CF_x$ couple. An exemplary capacitor comprises a tantalum anode and a ruthenium oxide cathode.

A terminal pin 28 connected to the cathode of an electrochemical cell or the anode of a capacitor extends through a glass-to-metal seal (GTMS) 30 fitted in the lid 16. The glass-to-metal seal 30 comprises a ferrule 32 supporting an insulating sealing glass or insulating ceramic 34 through which the terminal pin 28 extends. The sealing glass or ceramic 34 electrically isolates the terminal pin 28 from the ferrule 32. The ferrule 32 is welded into an opening in the lid 16 and, after the electrode assembly is housed in the container 14, the lid is welded to the open end of the container to provide the casing 12. An electrolyte (not shown) is then filled into the casing 12 through a fill port or opening 36 provided in the lid 16 to contact the electrode assembly. In its fully assembled condition shown in FIG. 1, a closure means 38 is sealed in the electrolyte fill port 36 to hermetically close the casing 12. Exemplary welding techniques include laser welding, resistance welding, arc welding, and magnetic pulse welding.

Titanium is a suitable material for the container 14, lid 16 and the ferrule 32 of the GTMS 30. In addition to titanium, suitable materials for the container 14, lid 16 and the ferrule 32 include stainless steel, mild steel, nickel-plated mild steel, nickel, aluminum, tantalum, but not limited thereto, so long as the metallic material is compatible for use with the other cell components.

Exemplary electrically insulating sealing glasses 34 residing between the terminal pin 28 and the ferrule 32 for the GTMS 30 include, but are not limited to, Ferro IP510, Corning 1890, Schott 8422 and Schott 8629. Alumina is a suitable ceramic.

Suitable materials for the terminal pin 28 include molybdenum, tantalum, tungsten, and combinations thereof.

External connection of the power source to a load is provided by the terminal pin 28 and by a contact region comprising the lid 16 or the entire conductive casing 12, which are insulated from the terminal pin 28 by the glass-to-metal seal 30.

Figure 2:
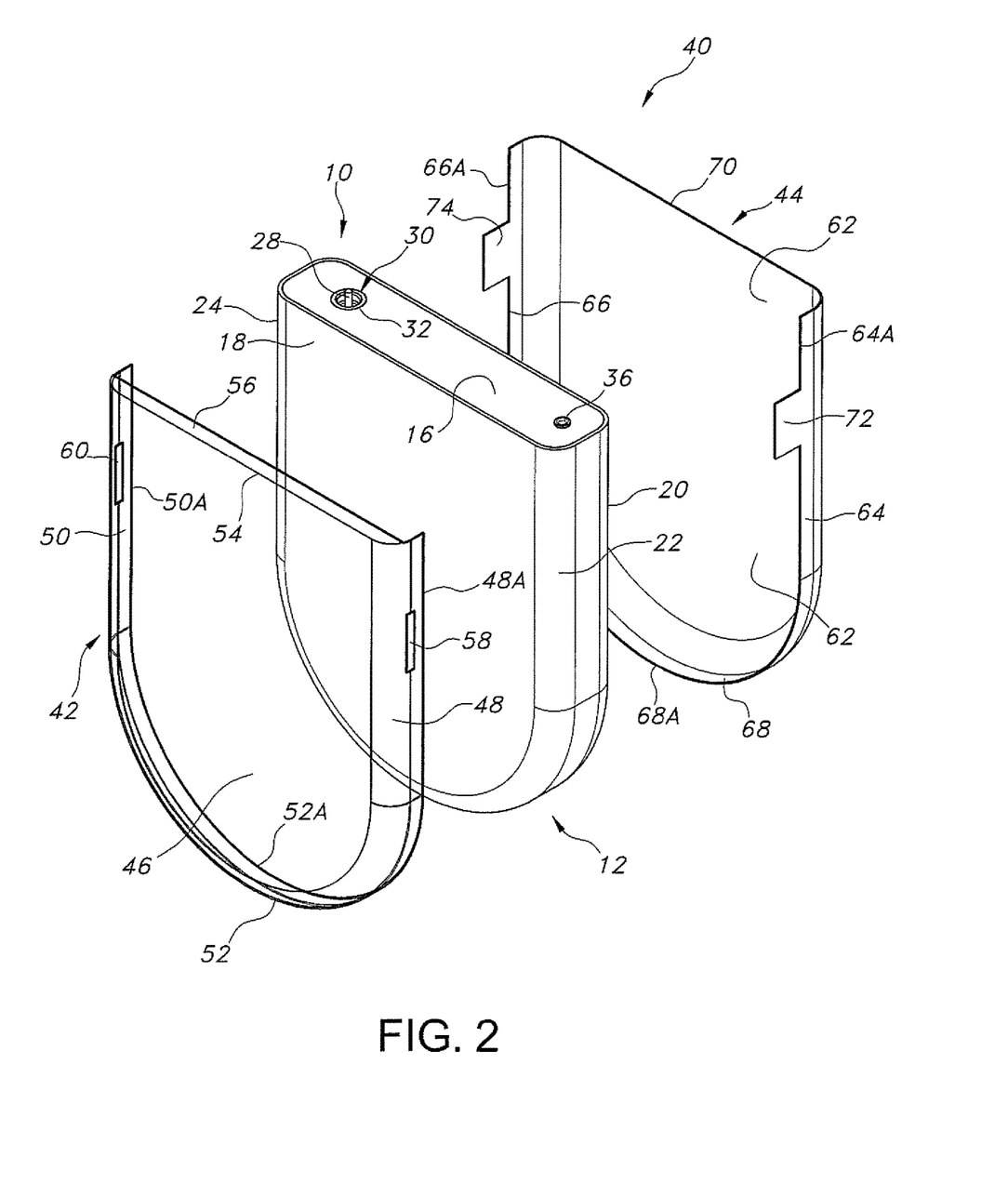
FIG. 2 is an exploded view of the electrochemical cell 10 shown in FIG. 1 prior to an exemplary polymeric film cover assembly 40 being contacted the exterior surface of the cell casing 12.

FIG. 2 is an exploded view of the power source 10 shown in FIG. 1 prior to an exemplary embodiment of a polymeric film cover assembly 40 being contacted to the exterior surface of the casing 12. The polymeric film cover assembly 40 comprises a shallow-formed first or front shaped-cover 42 that is connectable to a shallow-formed second or back shaped-cover 44 to substantially envelope the casing 12. The front cover 42 has a shape that matches that of the front-face wall 18 and front portions of the right and left curved end walls 22, 24 and the curved bottom wall 26 of the container 14 and a front portion of the lid 16 for the casing 12. The front cover 42 comprises a planar front major-face wall 46 that extends to a curved right front sidewall 48, a curved left front sidewall 50 and a curved intermediate bottom front wall 52. The curved bottom front wall 52 extends to and meets with the curved right and left front sidewalls 48 and 50. Further, the curved right front sidewall 48, the curved bottom front wall 52 and the curved left front sidewall 50 extend to respective edges 48A, 52A and 50A spaced from the planar front major-face wall 46. These edges 48A, 50A and 52A reside along a first imaginary plane that is co-planar with the plane of the front major-face wall 46.

The curved right and left front sidewalls 48, 50 and the front major-face wall 46 extend upwardly to an upper edge 54 residing along a second imaginary plane that is substantially perpendicular to the first imaginary plane of the edges 48A, 50A and 52A. A front polymeric web 56 extends outwardly along the second imaginary plane and away from the front major-face wall 46 at the upper edge 54, however, the web 56 ends spaced from the first imaginary plane of the edges 48A, 50A and 52A of the curved right and left front sidewalls 48, 50 and the curved bottom front wall 52.

A right slit 58 is provided in the curved right front sidewall 48 and a left slit 60 is provided in the curved left front sidewall 50.

The back shaped-cover 44 of the cover assembly 40 has a shape that matches that of the back-face wall 20 and back portions of the right and left curved end walls 22, 24 and the curved bottom wall 26 of the container 14 for the casing 12. The back cover 44 comprises a planar back-face wall 62 that extends to a curved right back sidewall 64, a curved left back sidewall 66 and a curved intermediate bottom back wall 68. The curved bottom back wall 68 extends to and meets with the curved right and left back sidewalls 64 and 66. Further, the curved right back sidewall 64, the curved bottom back wall 68 and the curved left back sidewall 66 extend to respective edges 64A, 68A and 66A spaced from the planar back major-face wall 62. These edges 64A, 66A and 68A reside along a third imaginary plane that is co-planar with the plane of the back major-face wall 62.

The curved right and left back sidewalls 64, 66 and the back major-face wall 62 extend upwardly to an upper edge 70 residing along a fourth imaginary plane that is substantially perpendicular to the third imaginary plane of the edges 64A, 66A and 68A.

A right tab 72 extends outwardly from the curved right back sidewall 64 and away from the back major-face wall 62. Similarly, a left tab 74 extends outwardly from the curved left back sidewall 66 and away from the back major-face wall 62.

When the first or front-shaped cover 42 is contacted to the front face wall 18 of the casing 12 and the second or back-shaped cover 44 is contacted to the back face wall 20 of the casing 12 for the power source 10, the right tab 72 is received or inter-locked into the right slit 58 and the left tab 74 is received or inter-locked into the left slit 60 to connect and hold the shaped covers 42 and 44 together. Further, the edges 48A, 50A and 52A of the curved right and left front sidewalls 48, 50 and the curved bottom front wall 52 of the front cover 42 meet the edges 64A, 66A and 68A of the curved right and left back sidewalls 64, 66 and the curved bottom back wall 68 of the back cover 44 in an overlapping or butted relationship. If overlapping, either the front shaped-cover 42 is somewhat larger than the back shaped-cover 44 so that the edges 48A, 50A and 52A of the front cover 42 overlap the edges 64A, 66A and 68A of the back cover 44 or, the back cover 44 is somewhat larger than the front cover 42 with the edges 64A, 66A and 68A of the back cover overlapping the edges 48A, 50A and 52A of the front cover 42. In either embodiment, the outer surface of the casing 12 for the power source 10 is substantially enveloped in the polymeric film cover assembly 40. With the front and back-shaped covers 42 and 44 connected to each other, the front web 56 covers a front portion of the lid 16, leaving a back portion of the lid 16 uncovered.

Figure 3:
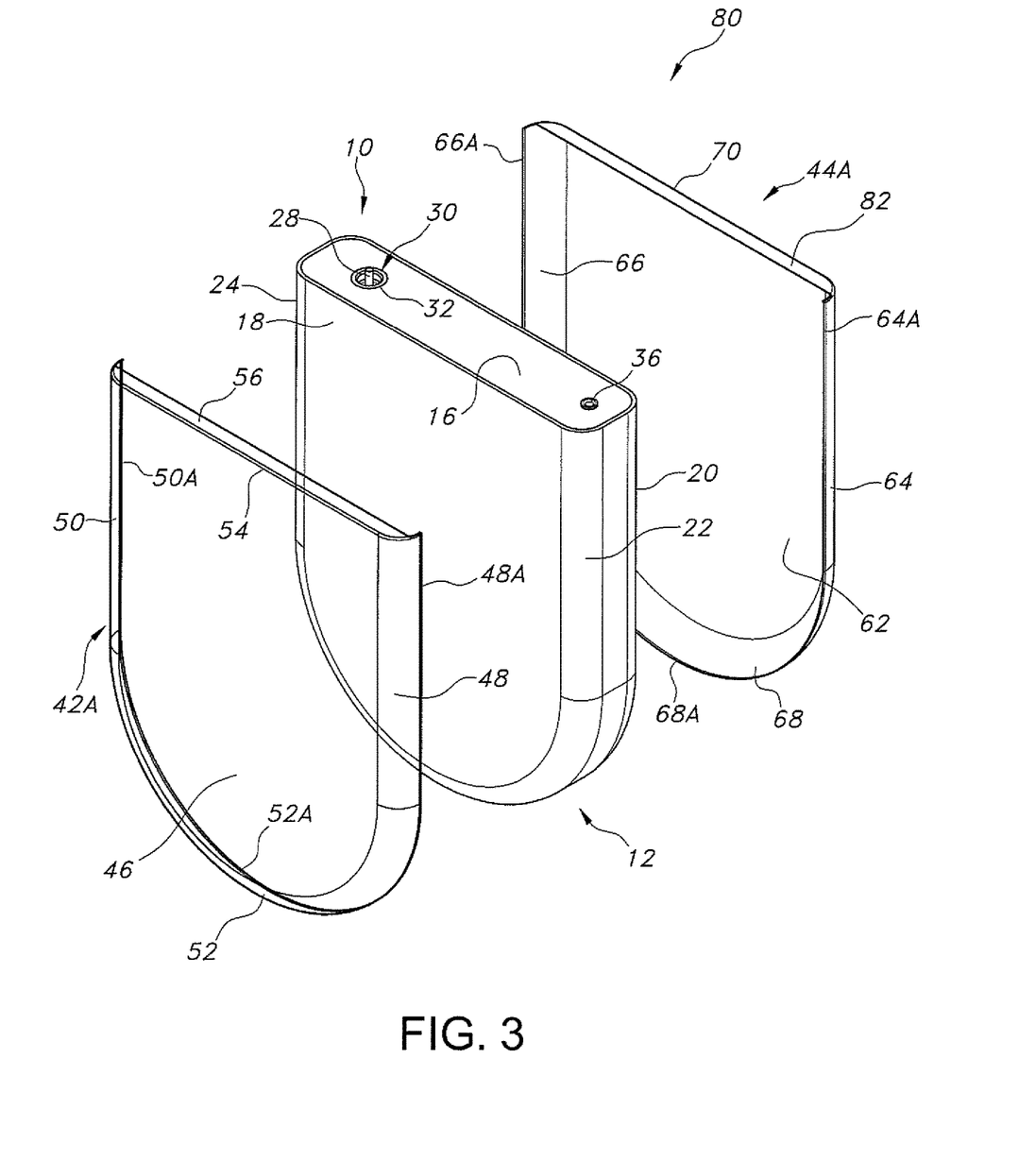
FIG. 3 is an exploded view of the electrochemical cell 10 shown in FIG. 1 prior to an exemplary polymeric film cover assembly 80 being contacted the exterior surface of the cell casing 12.

FIG. 3 is an exploded view of the power source 10 shown in FIG. 1 prior to another exemplary embodiment of a polymeric film cover assembly 80 being contacted to the exterior surface of the casing 12. The cover assembly 80 is similar to the cover assembly 40 illustrated in FIG. 2 except that the shallow-formed front shaped-cover 42A does not have the slits 58, 60 and the shallow-formed back shaped-cover 44A does not have the tabs 72, 74. Further, a back polymeric web 82 extends outwardly from the upper edge 70, away from the back major-face wall 62 and along the fourth imaginary plane. The web 82 ends spaced from the third imaginary plane of the edges 64A, 66A and 68A of the curved right and left back sidewalls 64, 66 and the curved bottom back wall 68.

With the front and back-shaped covers 42A and 44A contacted to the respective front and back face walls 18, 20 of the container 14 for the casing 12 and being connected to each other in the previously described butted or overlapping relationship of their respective edges 48A, 50A, 52A and 64A, 66A, 68A, the front web 56 covers a front portion of the lid 16 and the back web 82 covers a back portion of the lid. Preferably, the outer edges of the webs 56, 82 meet each other in an overlapping or butted relationship to completely cover the lid 16, but that is not necessary. A portion of the lid 16 can be left uncovered.

Figure 4:
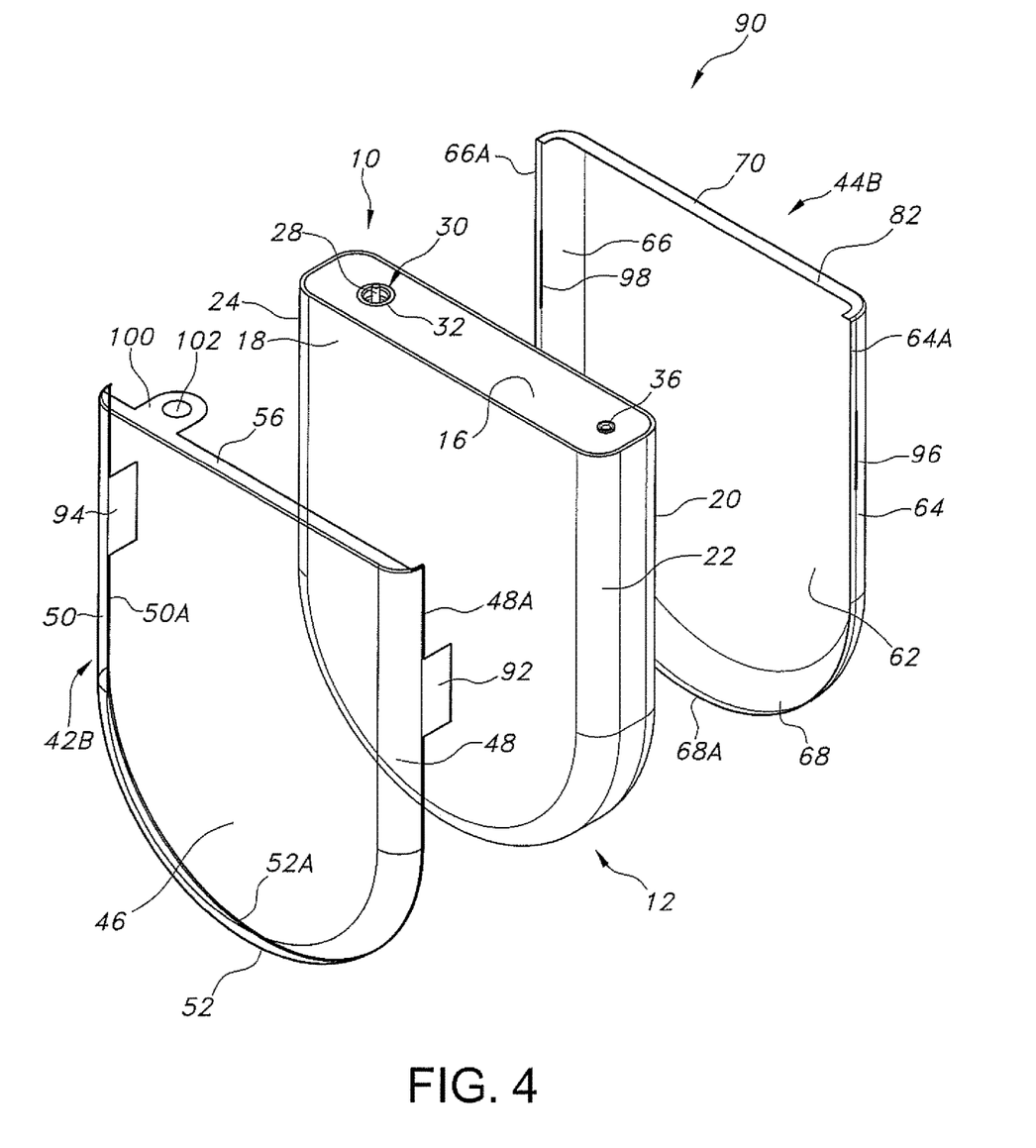
FIG. 4 is an exploded view of the electrochemical cell 10 shown in FIG. 1 prior to another exemplary embodiment of a polymeric film cover assembly 90 being contacted the exterior surface of the cell casing 12.

FIG. 4 is an exploded view of the power source 10 shown in FIG. 1 prior to another exemplary embodiment of a polymeric film cover assembly 90 being contacted to the exterior surface of the casing 12. The cover assembly 90 is similar to the cover assembly 40 illustrated in FIG. 2 except that the back polymeric web 82 extends outwardly from the upper edge 70 of the shallow-formed back shaped-cover 44, away from the back major-face wall 62 and along the fourth imaginary plane. The web 82 ends spaced from the third imaginary plane of the edges 64A, 66A and 68A of the curved right and left back sidewalls 64, 66 and the curved bottom back wall 68.

The front shaped cover 42B also has a right tab 92 that extends outwardly from the curved right front sidewall 48 and away from the front major-face wall 46. Similarly, a left tab 94 extends outwardly from the curved left front sidewall 50 and away from the front major-face wall 46. A right slit 96 is provided in the curved right back sidewall 64 and a left slit 98 is provided in the curved left back sidewall 66.

In a similar manner as describe above with respect to the cover assembly 40 shown in FIG. 2, when the first or front-shaped cover 42B is contacted to the front face wall 18 of the container 14 for the casing 12 and the second or back-shaped cover 44B is contacted to the back-face wall 20 of the container 14, the right tab 92 is received or inter-locked in the right slit 96 and the left tab 94 is received or inter-locked in the left slit 98 to connect and hold the shaped covers 42B and 44B together.

As with the cover assembly 40 shown in FIG. 2, the edges 48A, 50A and 52A of the curved right and left front sidewalls 48, 50 and the curved bottom front wall 52 of the front cover 42B meet the edges 64A, 66A and 68A of the curved right and left back sidewalls 64, 66 and the curved bottom back wall 68 of the back cover 44B in an overlapping or butted relationship. If overlapping, either the front shaped-cover 42B is somewhat larger than the back shaped-cover 44B so that the edges 48A, 50A and 52A of the front cover 42B overlap the edges 64A, 66A and 68A of the back cover 44B or, the back cover 44B is somewhat larger than the front cover 42B with the edges 64A, 66A and 68A of the back cover overlapping the edges 48A, 50A and 52A of the front cover 42B. In either embodiment, the outer surface of the casing 12 for the power source 10 is substantially enveloped in the polymeric film cover assembly 90. With the front and back-shaped covers 42B and 44B connected to each other, the front web 56 covers a front portion of the lid 16 and the back web 82 covers a back portion of the lid.

Further, an upper tab 100 extends outwardly from the upper web 56. The tab 100 is provided with an opening 102. With the front and back-shaped covers 42B and 44B con-tacted to the respective front and back face walls 18, 20 of the container 14 for the casing 12 and being connected to each other with the previously described tabs 92, 94 being mated to the respective slots 96, 98 and with the butted or overlapping relationship of their respective edges 48A, 50A, 52A and 64A, 66A, 68A, the front web 56 covers a front portion of the lid 16, the back web 82 covers a back portion of the lid, and the upper tab 100 is aligned with and covers the GTMS 30. The opening 102 provides a space for the terminal pin 28 to extends upwardly, through the upper tab 100.

Figure 5:
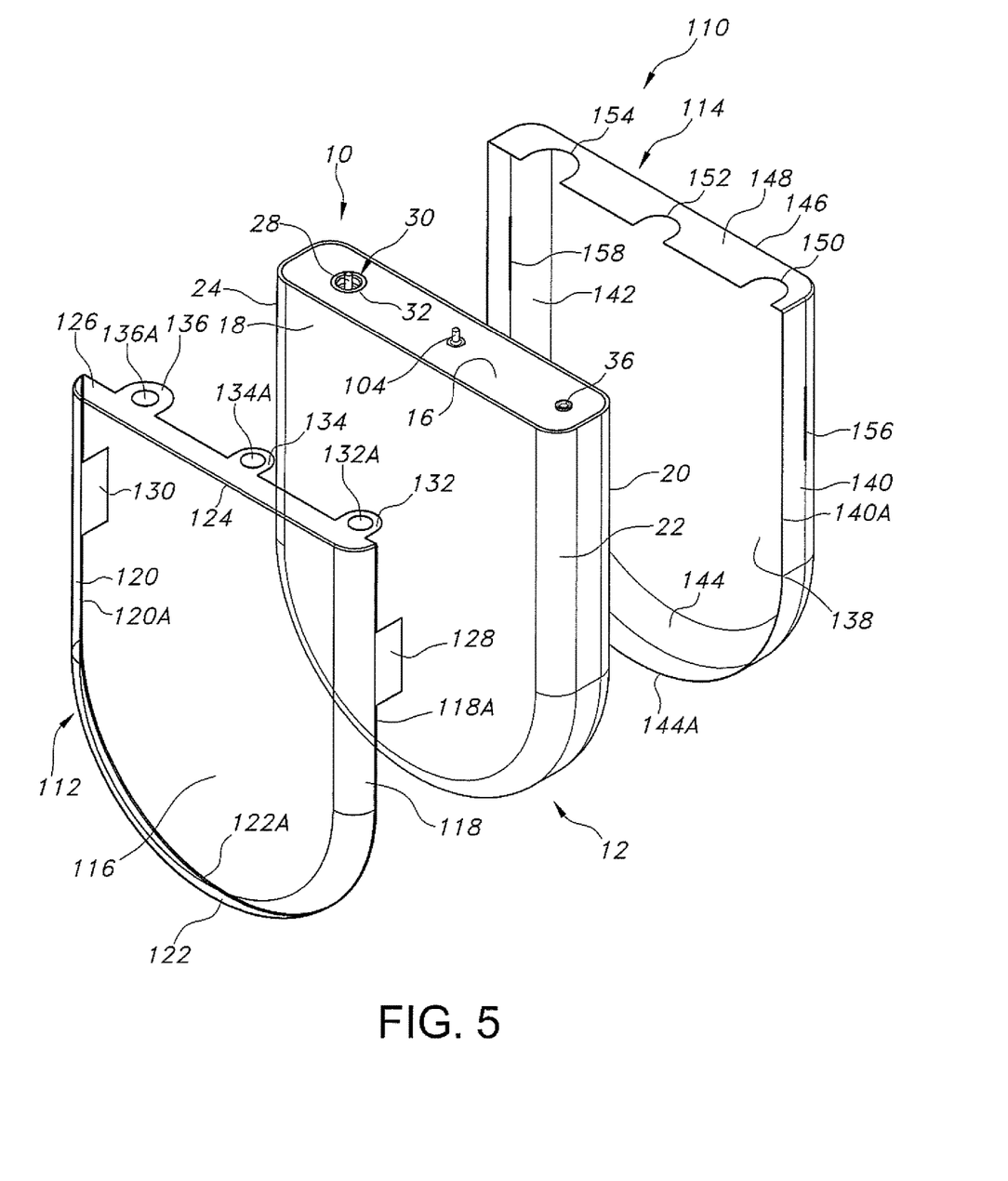
FIG. 5 is an exploded view of the electrochemical cell 10 prior to another exemplary embodiment of a polymeric film cover assembly 110 being contacted the exterior surface of the cell casing 12.

FIG. 5 is an exploded view of the power source 10 shown in FIG. 1 with the addition of a second terminal pin 104 connected directly to the lid 16 of the casing 12. Terminal pin 104 is provided as a structure that makes it easy for the power source 10 to be connected to a load. For example, in an electrochemical cell having a case-negative design, the terminal pin 28 of the GTMS 30 is the positive polarity connection to the cathode and the lid terminal pin 104 is the negative polarity connection to the anode. The power source 10 is illustrated prior to an exemplary embodiment of a polymeric film cover assembly 110 being contacted to the exterior surface of the casing 12.

The polymeric film cover assembly 110 comprises a shallow-formed first or front shaped-cover 112 that is con-nectable to a shallow-formed second or back shaped-cover 114 to substantially envelope the casing 12. The front cover 112 has a shape that matches that of the front-face wall 18 and front portions of the right and left curved end walls 22, 24 and the curved bottom wall 26 of the container 14 and a front portion of the lid 16 for the casing 12. The front cover 112 comprises a planar front major-face wall 116 that extends to a curved right front sidewall 118, a curved left front sidewall 120 and a curved intermediate bottom front wall 122. The curved bottom front wall 122 extends to and meets with the curved right and left front sidewalls 118 and 120. Further, the curved right front sidewall 118, the curved bottom front wall 122 and the curved left front sidewall 120 extend to respective edges 118A, 122A and 120A spaced from the planar front major-face wall 116. These edges 118A, 120A and 122A reside along a fifth imaginary plane that is co-planar with the plane of the front major-face wall 116.

The curved right and left front sidewalls 118, 120 and the front major-face wall 116 extend upwardly to an upper edge 124 residing along a sixth imaginary plane that is substan-tially perpendicular to the fifth imaginary plane of the edges 118A, 120A and 122A. A front polymeric web 126 extends outwardly along the sixth imaginary plane and away from the front major-face wall 116 at the upper edge 124. The web 126 extends to the fifth imaginary plane of the edges 118A, 120A and 122A of the curved right and left front sidewalls 118, 120 and the curved bottom front wall 122.

A right tab 128 extends outwardly from the curved right front sidewall 118 and away from the front major-face wall 116. Similarly, a left tab 130 extends outwardly from the curved left front sidewall 120 and away from the front major-face wall 116.

Further, a first upper tab 132, a second upper tab 134 and a third upper tab 136 extend outwardly from the upper web 126. The tabs 132, 134 and 136 are provided with respective openings 132A, 134A and 136A, the significance of which will be described hereinafter.

The back shaped-cover 114 of the cover assembly 110 has a shape that matches that of the back-face wall 20 and back portions of the right and left curved end walls 22, 24 and the curved bottom wall 26 of the container 14 and a back portion of the lid 16 for the casing 12. The back cover 114 comprises a planar back-face wall 138 that extends to a curved right back sidewall 140, a curved left back sidewall 142 and a curved intermediate bottom back wall 144. The curved bottom back wall 144 extends to and meets with the curved right and left back sidewalls 140 and 142. Further, the curved right back sidewall 140, the curved bottom back wall 144 and the curved left back sidewall 142 extend to respective edges 140A, 144A and 142A spaced from the planar back major-face wall 138. These edges 140A, 142A and 144A reside along a seventh imaginary plane that is co-planar with the plane of the back major-face wall 138.

The curved right and left back sidewalls 140, 142 and the back major-face wall 138 extend upwardly to an upper edge 146 residing along an eighth imaginary plane that is substantially perpendicular to the seventh imaginary plane of the edges 140A, 142A and 144A. A back web 148 extends outwardly along the eighth imaginary plane and away from the back major-face wall 138 at the upper edge 146. The back web 148 extends to the seventh imaginary plane of the edges 140A, 142A and 144A of the curved right and left front sidewalls 140, 142 and the curved bottom front wall 144. The back web 148 is provided with a first inlet 150, a second inlet 152 and a third inlet 154.

A right slit 156 is provided in the curved right back sidewall 140 and a left slit 158 is provided in the curved left back sidewall 142.

When the first or front-shaped cover 112 is contacted to the front face wall 18 of the casing 12 and the second or back-shaped cover 114 is contacted to the back face wall 20 of the casing 12 for the power source 10, the right tab 128 is received or inter-locked into the right slit 156 and the left tab 130 is received or inter-locked into the left slit 158 to connect and hold the shaped covers 112 and 114 together. Further, the edges 118A, 120A and 122A of the curved right and left front sidewalls 118, 120 and the curved bottom front wall 122 of the front cover 112 meet the edges 140A, 142A and 144A of the curved right and left back sidewalls 140, 142 and the curved bottom back wall 144 of the back cover 114 in an overlapping or butted relationship. If overlapping, either the front shaped-cover 112 is somewhat larger than the back shaped-cover 114 so that the edges 118A, 120A and 122A of the front cover 112 overlap the edges 140A, 142A and 144A of the back cover 114 or, the back cover 114 is somewhat larger than the front cover 112 with the edges 140A, 142A and 144A of the back cover overlapping the edges 118A, 120A and 122A of the front cover 112. In either embodiment, the outer surface of the casing 12 for the power source 10 is substantially enveloped in the polymeric film cover assembly 110.

Further, with the front and back-shaped covers 112 and 114 connected to each other, the front web 126 covers a front portion of the lid 16 and the back web 148 covers a back portion of the lid. The opening 136A in the first upper tab 132 extending outwardly from the front web 126 is aligned with the electrolyte fill port 36, the second terminal pin 104 connected to the lid 16 is received in the opening 134A in the second upper tab 134 and the terminal pin 128 of the GTMS 130 is received in the opening 136A of the third tab 136. Then, the first upper tab 132 is received in the first inlet 150 in the back web 148, the second upper tab 134 is received in the second inlet 152 and the third upper tab 136 is received in the third inlet 154 of the back web.

Thus, various exemplary embodiments of polymeric film cover assemblies 40, 80, 90 and 110 according to the present invention have been described. The cover assemblies 40, 80, 90 and 110 are readily adapted to insulate the exterior surface of a power source such as an electrochemical cell or a capacitor. When the power source is incorporated into an implantable medical device to power the device, the cover assemblies 40, 80, 90 and 110 readily form-fit to the exterior shape of the power source to provide the necessary insulation while maintaining the desired power source thickness.

Thermo-formed clear polyester film, which is more transparent than polyimide film, is a suitable polymeric material. Thermo-formed clear polyester film is beneficial because it allows for the outer surface of the power source to be visible for inspection of the surface finish, markings, labels, for reading of a barcode or ID matrix, and the like. Polyester film is also readily shaped to selectively cover complex geometries while leaving features, such as the GTMS 30 and terminal pin 104 shown in FIG. 5 uncovered. Polyester films can also be shaped to include features such as edges, flaps and holes to thread thru-pins that will later be used to assist with proper alignment of the power source inside the implantable medical device.

It is appreciated that various modifications to the inventive concepts described herein may be apparent to those of ordinary skill in the art without departing from the spirit and scope of the present invention as defined by the appended claims.

What is claimed is:

1. An electrochemical power source assembly, comprising:
   a) an electrochemical power source comprising a casing housing an anode and a cathode in electrochemical association with each other, the casing having an exterior surface with an exterior surface area;
   b) a polymeric film cover assembly, comprising:
      i) a first shaped-cover of a polymeric film configured to cover a first portion of the exterior surface of the casing; and
      ii) a second shaped-cover of the polymeric film configured to cover a second portion of the exterior surface of the casing,
      iii) wherein the first shaped-cover has spaced-apart slits, and the second shaped-cover has spaced-apart tabs that are received in a respective one of the slits to connect the first and second shaped covers to each other contacting the casing.

2. The assembly of claim 1, wherein the polymeric film of the cover assembly is a polyester film.

3. The assembly of claim 1, wherein the casing comprises an open-ended container closed by a lid, and wherein with the first and second shaped-covers contacting the casing and connected to each other, only a first portion of the lid is contacted by the cover assembly, leaving a second portion of the lid uncovered.

4. The assembly of claim 1, wherein the polymeric film cover assembly covers greater than 50% of the exterior surface area of the casing.

5. The assembly of claim 1, wherein the electrochemical power source has a terminal pin connected to one of the anode and the cathode and extending outwardly from a glass-to-metal-seal connected to the casing, and wherein the polymeric film cover assembly covers the entire exterior surface area of the casing, leaving only the terminal pin uncovered.

6. The assembly of claim 1, wherein the electrochemical power source has a terminal pin connected to one of the anode and the cathode and extending outwardly from a glass-to-metal-seal connected to the casing, and an electrolyte fill port, and wherein the polymeric film cover assembly covers the entire exterior surface area of the casing, leaving only the terminal pin and the electrolyte fill port uncovered.

7. The assembly of claim 1, wherein the electrochemical power source has a first terminal pin connected to one of the anode and the cathode and extending outwardly from a glass-to-metal-seal connected to the casing, and a second terminal pin connected to the casing and serving as a terminal for the other of the anode and the cathode not connected to the first terminal pin, and wherein the polymeric film cover assembly covers the entire exterior surface area of the casing, leaving only the first and second terminal pins uncovered.

8. The assembly of claim 1, wherein the electrochemical power source has a first terminal pin connected to one of the anode and the cathode and extending outwardly from a glass-to-metal-seal connected to the casing, a second terminal pin connected to the casing and serving as a terminal for the other of the anode and the cathode not connected to the first terminal pin, and an electrolyte fill port, and wherein the polymeric film cover assembly covers the entire exterior surface area of the casing, leaving only the first and second terminal pins and the electrolyte fill port uncovered.

9. The assembly of claim 1, wherein, with the spaced-apart tabs of the second shaped-cover received in a respective one of the spaced-apart slits of the first shaped-cover, the first and second shaped-covers are connected to each other in an overlapping or butted relationship to substantially cover the exterior surface area of the casing.

10. The assembly of claim 1, wherein the casing comprises opposed front and back major face walls joined to opposed end walls and a bottom wall, and wherein the first shaped-cover comprises a first major face wall extending to a first bottom wall, the first bottom wall meeting with spaced-apart first right and left edge walls, and wherein the second shaped-cover comprises a second major face wall extending to a second bottom wall, the second bottom wall meeting with spaced-apart second right and left edge walls, and wherein the first shaped-cover is configured to cover the first major face wall and front portions of the bottom wall and the spaced-apart first right and left edge walls of the casing, and wherein the second shaped-cover is configured to cover the second major face wall and back portions of the bottom wall and the spaced-apart right and left edge walls of the casing to substantially cover the exterior surface area of the casing.

11. The assembly of claim 10, wherein the first bottom wall and the first right and left edge walls of the first shaped-cover are curved, and wherein the second bottom wall and the second right and left edge walls of the second shaped-cover are curved.

12. The assembly of claim 1, wherein the electrochemical power source has a terminal pin connected to one of the anode and the cathode and extending outwardly from a glass-to-metal-seal connected to the casing, and wherein a third tab extends outwardly from a first upper web of the first-shaped covers, the third tab having a third opening through which the terminal pin extends, and wherein a second upper web extends outwardly from the second-shaped cover, the second upper web having an inlet that receives the third tab with the first and second shaped-covers contacting the casing to substantially cover the exterior surface area of the casing.

13. The assembly of claim 12, wherein a second terminal pin connected to the casing serves as a terminal for the other of the anode and the cathode not connected to the first terminal pin, and wherein a fourth tab extends outwardly from the first upper web of the first-shaped covers, the fourth tab having a fourth opening through which the second terminal pin extends, and wherein the second upper web has a second inlet that receives the fourth tab with the first and second shaped-covers contacting the casing to substantially cover the exterior surface area of the casing.

14. The assembly of claim 13, wherein the casing has an electrolyte fill port, and wherein a fifth tab extends outwardly from the first upper web of the first-shaped cover, the fifth tab having a fifth opening aligned with the electrolyte fill port, and wherein the second upper web has a fifth inlet that receives the fifth tab with the first and second shaped-covers contacting the casing to substantially cover the exterior surface area of the casing.

15. An electrochemical power source assembly, comprising:
   a) an electrochemical power source comprising:
      i) a casing housing an anode and a cathode in electrochemical association with each other, the casing having an exterior surface with an exterior surface area;
      ii) a first terminal pin connected to one of the anode and the cathode and extending outwardly from a glass-to-metal-seal connected to the casing; and
      iii) a second terminal pin connected to the casing and serving as a terminal for the other of the anode and the cathode not connected to the first terminal pin;
   b) a polymeric film cover assembly, comprising:
      i) a first shaped-cover of a polymeric film configured to cover a first portion of the exterior surface of the casing, wherein the first shaped-cover has a first outwardly extending upper web;
      ii) a second shaped-cover of the polymeric film configured to cover a second portion of the exterior surface of the casing, wherein the second shaped-cover has a second outwardly extending upper web;
      iii) a first tab extending outwardly from the first upper web of the first-shaped cover, the first tab having a first opening through which the first terminal pin extends, wherein a first inlet in the second web receives the first tab; and
      iv) a second tab extending outwardly from the first upper web of the first-shaped cover, the second tab having a second opening through which the second terminal pin extends, wherein a second inlet in the second web receives the second tab,
   c) wherein, one of the first and second shaped-covers has a pair of spaced-apart slits, and the other of the first and second shaped-covers has a pair of spaced-apart tabs that are received in a respective one of the slits to connect the first and second shaped covers to each other contacting the casing.

16. The assembly of claim 15, wherein the polymeric film of the cover assembly is a polyester film.

17. The assembly of claim 15, wherein the polymeric film cover assembly covers greater than 50% of the exterior surface area of the casing.

18. The assembly of claim 15, wherein the polymeric film cover assembly covers the entire exterior surface area of the casing, leaving only the first and second terminal pins uncovered.

19. The assembly of claim 15, wherein, with the spaced-apart tabs of the other of the first and second shaped-covers received in a respective one of the spaced-apart slits of the one of the first and second shaped-covers, the first and second shaped-covers are connected to each other in an overlapping or butted relationship to substantially cover the exterior surface area of the casing.

20. An electrochemical power source assembly, comprising:
   a) an electrochemical power source comprising a casing housing an anode and a cathode in electrochemical association with each other, the casing having an exterior surface with an exterior surface area; and
   b) a polyester film cover assembly, comprising:
      i) a first shaped-cover of a polyester film configured to cover a first portion of the exterior surface of the casing; and
      ii) a second shaped-cover of the polyester film configured to cover a second portion of the exterior surface of the casing,
      iii) wherein, with the first and second shaped-covers contacting the casing, the first and second shaped-covers are connected to each other in an overlapping or butted relationship to substantially cover the exterior surface area of the casing.

* * * * *